US008501947B2

(12) United States Patent
Treppendahl et al.

(10) Patent No.: US 8,501,947 B2
(45) Date of Patent: Aug. 6, 2013

(54) MANUFACTURE OF 4-((1R,3S)-6-CHLORO-3-PHENYL-INDAN-1-YL)-1,2,2-TRIMETHYL-PIPERAZINE AND 1-((1R,3S)-6-CHLORO-3-PHENYL-INDAN-1-YL)-3,3-DIMETHYL-PIPERAZINE

(75) Inventors: Svend Treppendahl, Virum (DK); Allan Carsten Dahl, Nyrup (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 13/382,378

(22) PCT Filed: Jul. 7, 2010

(86) PCT No.: PCT/DK2010/050177
§ 371 (c)(1),
(2), (4) Date: Feb. 22, 2012

(87) PCT Pub. No.: WO2011/003423
PCT Pub. Date: Jan. 13, 2011

(65) Prior Publication Data
US 2012/0142923 A1    Jun. 7, 2012

Related U.S. Application Data

(60) Provisional application No. 61/223,551, filed on Jul. 7, 2009.

(30) Foreign Application Priority Data

Jul. 7, 2009    (DK) .................................. 2009 00835

(51) Int. Cl.
*C07D 241/04*    (2006.01)

(52) U.S. Cl.
USPC ......................................................... 544/403

(58) Field of Classification Search
USPC ......................................................... 544/403
See application file for complete search history.

(56) References Cited

U.S. PATENT DOCUMENTS
2008/0153847 A1    6/2008    Dahl et al.

FOREIGN PATENT DOCUMENTS
WO    WO 2005016900 A1 *    2/2005
WO    WO 2006086985 A1 *    8/2006

OTHER PUBLICATIONS

International Union of Pure and Applied Chemisty (IUPAC). "Handbook of Pharmaceutical Salts: Properties, Selection, and Use." Stahl, P. Heinrich, Wermuth, C.G., editors. Copyright 2002.*
Fogassy, E., et al. "Optical resolution methods." Organic & Biomolecular Chemistry. (2006), vol. 4, pp. 3011-3030.*
Bogeso K P et al, 1995, Enhanced D1 Affinity in a Series of Piperazine Ring Substituted 1-Piperazino-3-Arylindans with Potential Atypical Antipsychotic Activity, J. Med. Chem. 38(22):4380-4392.

* cited by examiner

*Primary Examiner* — Noble Jarrell
*Assistant Examiner* — John S Kenyon
(74) *Attorney, Agent, or Firm* — Mary Catherine Di Nunzio

(57) ABSTRACT

The present invention relates to a process for the manufacture of 4-((1R,3S)-6-Chloro-3-phenyl-indan-1-yl)-1,2,2-trimethyl-piperazine or a pharmaceutically acceptable salt thereof and a process for the manufacture of 1-((1R,3S)-6-Chloro-3-phenyl-indan-1-yl)-3,3-dimethyl-piperazine or a pharmaceutically acceptable salt thereof.

18 Claims, No Drawings

US 8,501,947 B2

MANUFACTURE OF 4-((1R,3S)-6-CHLORO-3-PHENYL-INDAN-1-YL)-1,2,2-TRIMETHYL-PIPERAZINE AND 1-((1R,3S)-6-CHLORO-3-PHENYL-INDAN-1-YL)-3,3-DIMETHYL-PIPERAZINE

CROSS-REFERENCE TO RELATED APPLICATIONS

This application is a 371 National Phase of PCT/DK2010/050177, filed Jul. 7, 2010, which claims priority under 35 U.S.C. §119(e) to U.S. Provisional Patent Application Ser. No. 61/223,551, filed Jul. 7, 2009. The entirety of each of the aforementioned applications is hereby incorporated by reference.

FIELD OF THE INVENTION

The present invention relates to resolvation methods for manufacture of 4-((1R,3S)-6-Chloro-3-phenyl-indan-1-yl)-1,2,2-trimethyl-piperazine and 1-((1R,3S)-6-Chloro-3-phenyl-indan-1-yl)-3,3-dimethyl-piperazine and pharmaceutically acceptable salts thereof.

BACKGROUND

The compounds of the present invention 4-((1R,3S)-6-Chloro-3-phenyl-indan-1-yl)-1,2,2-trimethyl-piperazine (I) and 1-((1R,3S)-6-Chloro-3-phenyl-indan-1-yl)-3,3-dimethyl-piperazine (II) hereinafter referred to as Compound (I) and (II) have the respective molecular structures depicted below.

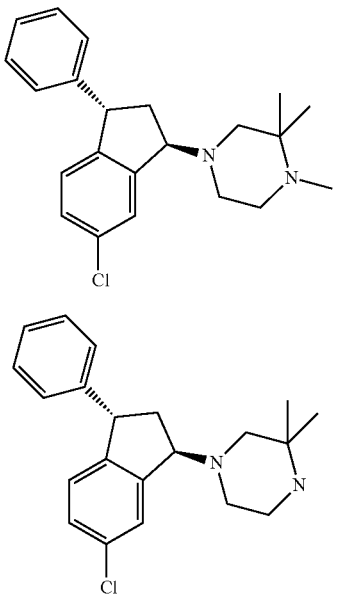

A group of trans isomers of 3-aryl-1-(1-piperazinyl)indanes substituted in the 2- and/or 3-position of the piperazine ring has been described in WO 93/22293 and in Klaus P. Bøgesø, Drug Hunting, the Medicinal Chemistry of 1-piperazino-3-phenylindans and Related Compounds, 1998, ISBN 87-88085-10-4 (cf. e.g. compound 69 in table 3, p. 47 and in table 9A, p. 101). The compounds are described as having high affinity for dopamine $D_1$ and $D_2$ receptors and the 5-$HT_2$ receptor and are suggested to be useful for treatment of several diseases in the central nervous system, including schizophrenia.

Trans racemic 4-((6-Chloro-3-phenyl-indan-1-yl)-1,2,2-trimethyl-piperazine and trans racemic 1-(6-Chloro-3-phenyl-indan-1-yl)-3,3-dimethyl-piperazine may e.g. be synthesized analogously to the methods outlined in Bøgesø et al., J. Med. Chem., 1995, 38, p. 4380-4392 and in WO 93/22293. Manufacture of Compound (I) by resolvation of trans racemic 4-((6-Chloro-3-phenyl-indan-1-yl)-1,2,2-trimethyl-piperazine has been described by Bøgesø et al. in J. Med. Chem., 1995, 38, p. 4380-4392, see table 5, compound (−)-38. The process described comprises the use of (+)-ditoluoyl tartaric acid for resolvation in ethylacetate, and Compound (I) is isolated as the fumarate salt.

The synthesis of Compound (II) from optically pure starting materials has been described in WO 2005/016900, WO 2005/016901 and WO 2006/086984. Synthesis of Compound (I) from Compound (II) by N-alkylation is disclosed in WO 2005/016900 (p. 31, example 12). A crystalline hydrogen tartrate salt of Compound (II) has been disclosed in WO 2006/086985.

Bøgesø et al., J. Med. Chem., 1995, 38, p. 4380-4392 discloses that Compound (I) is a potent $D_1/D_2$ antagonists showing some $D_1$ selectivity in vitro while in vivo it is equipotent as $D_1$ and $D_2$ antagonist. The compound is also described as a potent 5-$HT_2$ antagonist and as having high affinity for $α_1$ adrenoceptors. As disclosed in WO 2005/016901 Compound (II) displays a similar receptor profile and pharmacological activity as Compound (I).

SUMMARY OF THE INVENTION

The present inventors have found that a high yield and a high enantiomeric excess of 4-((1R,3S)-6-Chloro-3-phenyl-indan-1-yl)-1,2,2-trimethyl-piperazine and 1-((1R,3S)-6-Chloro-3-phenyl-indan-1-yl)-3,3-dimethyl-piperazine can be obtained by resolvation of their respective racemates with a chiral salt-forming acid.

Accordingly, in one embodiment, the present invention provides a process for the manufacture of 4-((1R,3S)-6-Chloro-3-phenyl-indan-1-yl)-1,2,2-trimethyl-piperazine or a pharmaceutically acceptable salt thereof comprising the step of mixing trans 4-(6-chloro-3-phenyl-indan-1-yl)-1,2,2-trimethyl-piperazine and L-(+)-tartaric acid in a polar solvent to obtain 4-((1R,3S)-6-Chloro-3-phenyl-indan-1-yl)-1,2,2-trimethyl-piperazine or a pharmaceutically acceptable salt thereof.

In another embodiment, the present invention provides a process for the manufacture of 4-((1R,3S)-6-Chloro-3-phenyl-indan-1-yl)-1,2,2-trimethyl-piperazine or a pharmaceutically acceptable salt thereof comprising the step of precipitating a product from a solution comprising trans 4-(6-chloro-3-phenyl-indan-1-yl)-1,2,2-trimethyl-piperazine and L-(+)-tartaric acid, in a polar solvent to obtain 4-((1R,3S)-6-Chloro-3-phenyl-indan-1-yl)-1,2,2-trimethyl-piperazine or a pharmaceutically acceptable salt thereof.

In another embodiment, the present invention provides a process for the manufacture of 4-((1R,3S)-6-Chloro-3-phenyl-indan-1-yl)-1,2,2-trimethyl-piperazine or a pharmaceutically acceptable salt thereof comprising the steps of
a) mixing trans 4-(6-chloro-3-phenyl-indan-1-yl)-1,2,2-trimethyl-piperazine and L-(+)-tartaric acid in a polar solvent;
b) optionally heating the obtained mixture to an appropriate temperature to obtain a solution of the trans 4-(6-chloro-3-phenyl-indan-1-yl)-1,2,2-trimethyl-piperazine and L-(+)-tartaric acid;

c) cooling the solution obtained in b) until precipitation;
d) isolating the precipitate obtained in c);
e) optionally drying the precipitate obtained in d);
to obtain 4-((1R,3S)-6-Chloro-3-phenyl-indan-1-yl)-1,2,2-trimethyl-piperazine or a pharmaceutically acceptable salt thereof.

In another embodiment, the present invention relates to a compound which is 4-((1R,3S)-6-Chloro-3-phenyl-indan-1-yl)-1,2,2-trimethyl-piperazine L-(+)-tartrate.

In one embodiment, the present invention relates to a process for the manufacture of 1-((1R,3S)-6-Chloro-3-phenyl-indan-1-yl)-3,3-dimethyl-piperazine or a pharmaceutically acceptable salt thereof comprising the step of mixing trans 1-(6-chloro-3-phenyl-indan-1-yl)-3,3-dimethyl-piperazine with D-(−)-tartaric acid in a polar solvent to obtain 1-((1R,3S)-6-Chloro-3-phenyl-indan-1-yl)-3,3-dimethyl-piperazine or a pharmaceutically acceptable salt thereof.

In another embodiment, the present invention relates to a process for the manufacture of 1-((1R,3S)-6-Chloro-3-phenyl-indan-1-yl)-3,3-dimethyl-piperazine or a pharmaceutically acceptable salt thereof comprising the step of precipitating a product from a solution comprising trans 1-(6-chloro-3-phenyl-indan-1-yl)-3,3-dimethyl-piperazine and D-(−)-tartaric acid in a polar solvent to obtain 1-((1R,3S)-6-Chloro-3-phenyl-indan-1-yl)-3,3-dimethyl-piperazine or a pharmaceutically acceptable salt thereof.

In another embodiment, the present invention relates to a process for the manufacture of 1-((1R,3S)-6-Chloro-3-phenyl-indan-1-yl)-3,3-dimethyl-piperazine or a pharmaceutically acceptable salt thereof comprising the steps of
a) mixing trans 1-(6-chloro-3-phenyl-indan-1-yl)-3,3-dimethyl-piperazine and D-(−)-tartaric acid in a polar solvent;
b) optionally heating the obtained mixture to an appropriate temperature to obtain a solution of the trans 1-((6-chloro-3-phenyl-indan-1-yl)-3,3-dimethyl-piperazine and D-(−)-tartaric acid;
c) cooling the solution obtained in b) until precipitation;
d) isolating the precipitate obtained in c);
e) optionally drying the precipitate obtained in d);
to obtain 1-((1R,3S)-6-Chloro-3-phenyl-indan-1-yl)-3,3-dimethyl-piperazine or a pharmaceutically acceptable salt thereof.

DEFINITIONS

As described herein, Compound (I) and Compound (II) respectively, is intended to designate any form of the compound, such as the free base, pharmaceutically acceptable salts thereof, e.g. pharmaceutically acceptable acid addition salts, such as succinate and malonate salts, hydrates or solvates of the free base or salts thereof, as well as anhydrous forms, amorphous forms, or crystalline forms.

As described herein, the term "chiral salt-forming acid" is defined as an organic acid with at least one chiral carbon atom. "a chiral salt-forming acid of the present invention" is meant to indicate L-(+)-tartaric acid and D-(−)-tartaric acid.

As described herein the term "polar solvent" is defined as a liquid composed of polar molecules. Examples include water, alcohols such as ethanol and propanol, organic acids such as formic acid, ketones such as acetone, tetrahydrofurane and mixtures hereof.

As described herein "a pharmaceutically acceptable salt" of a compound of Formula I or II includes pharmaceutically acceptable acid addition salts. Acid addition salts include salts of inorganic acids as well as organic acids. Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like.

In the context of the present invention the terms "resolvation" and "resolution" are use interchangeably and describes a process by which a racemate is separated into its two enantiomers.

In the present context, heating to an "appropriate temperature" indicates that the composition is heated to a temperature suitable for obtaining a solution, such as above room temperature such as >40° C., such as >45° C., such as >50° C., such as >55° C., such as >60° C., such as >65° C., such as >70° C. limited by the reflux temperature of the solvent. Dependent on the solvent used "appropriate temperature" might indicate reflux temperature, i.e. the composition is heated to reflux.

In the present context, "reflux" is a technique involving the condensation of vapors and the return of this condensate to the system from which it originated.

In the present context, "recrystallization" is a procedure for purifying compounds. Recrystallization can be performed by e.g. single-solvent recrystallization, multi-solvent recrystallization or hot filtration-recrystallization.

In the present context, "yield" of a synthesis process represents the total yield of synthesis product, including the salts of both enantiomers relative to the theoretical amount of racemate salt.

In the present context, "enantiomeric excess" is abbreviated ee and defined as the absolute difference between the mole fractions of each enantiomer of a compound.

As used herein, the term "trans 4-(6-chloro-3-phenylindan-1-yl)-1,2,2-trimethyl-piperazine", i.e. without any specific indication of the enantiomer form (e.g. using (+) and (−), or using the R/S-convention, refers to a mixture of the two enantiomers, 4-((1R,3S)-6-chloro-3-phenylindan-1-yl)-1,2,2-trimethyl piperazine (I) and 4-((1S,3R)-6-chloro-3-phenylindan-1-yl)-1,2,2-trimethyl piperazine. However, in this context preferably the content of the enantiomer corresponding to that of Compound (I) is at least 30% of the mixture, such as at least 40% such as at least 50%, i.e. at least as the racemate. The same principle applies for "trans-1-(6-Chloro-3-phenyl-indan-1-yl)-3,3-dimethyl-piperazine".

As used herein, the term "trans racemic 4-((6-Chloro-3-phenyl-indan-1-yl)-1,2,2-trimethyl-piperazine" refers to the racemate. The same principle applies for "trans racemic 1-(6-Chloro-3-phenyl-indan-1-yl)-3,3-dimethyl-piperazine".

In the present context, a "racemate" is an optically inactive compound that has substantially equal amounts of S and R enantiomers of a chiral molecule.

DETAILED DESCRIPTION OF THE INVENTION

The present invention relates to a process for manufacture of 4-((1R,3S)-6-Chloro-3-phenyl-indan-1-yl)-1,2,2-trimethyl-piperazine (Compound (I)) comprising resolution of trans 4-((6-Chloro-3-phenyl-indan-1-yl)-1,2,2-trimethyl-piperazine with L-(+)-tartaric acid.

The present invention also relates to a process for manufacture of 1-((1R,3S)-6-Chloro-3-phenyl-indan-1-yl)-3,3- dimethyl-piperazine (Compound (II)) comprising resolvation of trans 1-((6-Chloro-3-phenyl-indan-1-yl)-3,3-dimethyl-piperazine with D-(−)-tartaric acid.

In brief, the present invention relates to processes wherein the racemate is mixed with a chiral salt-forming acid of the present invention in a polar solvent. The mixture may optionally be heated to an appropriate temperature to obtain a solution of the racemate and the chiral salt-forming acid. Subsequent precipitation of the enantiomers may be obtained e.g. by cooling or evaporation and the precipitate may be isolated and optionally dried. It is the experience of the inventors that recrystallisation of the precipitate may increase the enantiomeric excess. The choice of solvent and conditions for the resolvation process e.g. temperature and stoichiometry of the starting materials may be used to optimize the yield and enantiomeric excess of the desired enantiomer.

The resolution methods of the present invention have been found to provide a yield of at least >40% under certain circumstances up to about 90% which is strikingly higher than the yield obtained by the resolvation method described in Bøgesø et al., J. Med. Chem., 1995, 38, p. 4380-4392 wherein (+)-ditoluoyl tartaric acid is used for resolution of trans racemic 4-((6-Chloro-3-phenyl-indan-1-yl)-1,2,2-trimethyl-piperazine. Furthermore, the processes of the present invention are much more suitable for upscaling. The resolution with unsubstituted tartaric acid gives easy filterable crystals with a high speed of filtration and the possibility of washing the filter cake. The diastereomeric crystallisations are very efficient giving often enantiomeric purities up to ee values of 98% of the first crystallisation. In contrast, resolution with (+)-ditoluoyl tartaric acid by the present inventors resulted in a less filterable precipitate requiring more steps of recrystallization and thus, this method is not suitable for use in a production scale.

Trans racemic 4-((6-Chloro-3-phenyl-indan-1-yl)-1,2,2-trimethyl-piperazine was also attempted resolved with (+)-dibenzoyl tartaric acid, (+)-camphorsulfonic acid, (−)-mandelic acid and L-glutamic acid. However, these alternatives suffers from either poor ability to crystallize or, in cases where crystals were obtained, lack of enantiomeric excess of the desired enantiomer. Likewise, trans racemic 1-(6-Chloro-3-phenyl-indan-1-yl)-3,3-dimethyl-piperazine) was attempted resolved with (+)-ditoluoyl tartataric acid, (+)-dibenzoyl tartaric acid, (+)-camphorsulfonic acid, (−)-mandelic acid and L-glutamic acid with the same disadvantages.

In a first embodiment, the present invention relates to a process for the manufacture of 4-((1R,3S)-6-Chloro-3-phenyl-indan-1-yl)-1,2,2-trimethyl-piperazine or a pharmaceutically acceptable salt thereof comprising the step of mixing trans 4-(6-chloro-3-phenyl-indan-1-yl)-1,2,2-trimethyl-piperazine with L-(+)-tartaric acid in a polar solvent to obtain 4-((1R,3S)-6-Chloro-3-phenyl-indan-1-yl)-1,2,2-trimethyl-piperazine or a pharmaceutically acceptable salt thereof.

In a further embodiment, the mixture of trans 4-(6-chloro-3-phenyl-indan-1-yl)-1,2,2-trimethyl-piperazine and L-(+)-tartaric acid in a polar solvent is brought into conditions suitable for obtaining a solution of the trans 4-(6-chloro-3-phenyl-indan-1-yl)-1,2,2-trimethyl-piperazine and L-(+)-tartaric acid. Preferably, said mixture of trans 4-(6-chloro-3-phenyl-indan-1-yl)-1,2,2-trimethyl-piperazine and L-(+)-tartaric acid in a polar solvent is heated to an appropriate temperature to obtain a solution of the trans 4-(6-chloro-3-phenyl-indan-1-yl)-1,2,2-trimethyl-piperazine and L-(+)-tartaric acid.

In another embodiment, the present invention relates to a process for the manufacture of 4-((1R,3S)-6-Chloro-3-phenyl-indan-1-yl)-1,2,2-trimethyl-piperazine or a pharmaceutically acceptable salt thereof comprising the step of precipitating a product from a solution comprising trans 4-(6-chloro-3-phenyl-indan-1-yl)-1,2,2-trimethyl-piperazine and L-(+)-tartaric acid in a polar solvent to obtain 4-((1R,3S)-6-Chloro-3-phenyl-indan-1-yl)-1,2,2-trimethyl-piperazine or a pharmaceutically acceptable salt thereof.

In another embodiment, the present invention relates to a process for the manufacture of 4-((1R,3S)-6-Chloro-3-phenyl-indan-1-yl)-1,2,2-trimethyl-piperazine or a pharmaceutically acceptable salt thereof comprising the steps of
a) mixing trans 4-(6-chloro-3-phenyl-indan-1-yl)-1,2,2-trimethyl-piperazine and L-(+)-tartaric acid in a polar solvent;
b) optionally heating the obtained mixture to an appropriate temperature to obtain a solution of the trans 4-(6-chloro-3-phenyl-indan-1-yl)-1,2,2-trimethyl-piperazine and L-(+)-tartaric acid;
c) cooling the solution obtained in b) until precipitation;
d) isolating the precipitate obtained in c);
e) optionally drying the precipitate obtained in d);
to obtain 4-((1R,3S)-6-Chloro-3-phenyl-indan-1-yl)-1,2,2-trimethyl-piperazine or a p ubsequent step in which the precipitate is recrystallised after step d) or e).harmaceutically acceptable salt thereof. Optionally, the process comprises a s In a preferred embodiment, the trans 4-(6-chloro-3-phenyl-indan-1-yl)-1,2,2-trimethyl-piperazine used in the process for manufacture of 4-((1R,3S)-6-Chloro-3-phenyl-indan-1-yl)-1,2,2-trimethyl-piperazine is the trans racemic 4-(6-chloro-3-phenyl-indan-1-yl)-1,2,2-trimethyl-piperazine.

In one embodiment, 4-((1R,3S)-6-Chloro-3-phenyl-indan-1-yl)-1,2,2-trimethyl-piperazine L-(+)-tartrate is an intermediate or end product of the process. In a preferred embodiment, said 4-((1R,3S)-6-Chloro-3-phenyl-indan-1-yl)-1,2,2-trimethyl-piperazine L-(+)-tartrate is in a crystalline form.

In one embodiment, the present invention relates to a compound which is 4-((1R,3S)-6-Chloro-3-phenyl-indan-1-yl)-1,2,2-trimethyl-piperazine L-(+)-tartrate. In a preferred embodiment, said 4-((1R,3S)-6-Chloro-3-phenyl-indan-1-yl)-1,2,2-trimethyl-piperazine L-(+)-tartrate is in a crystalline form.

The present invention also relates to a process for manufacture of 1-((1R,3S)-6-Chloro-3-phenyl-indan-1-yl)-3,3-dimethyl-piperazine (Compound (II)) by resolution of trans 1-(6-Chloro-3-phenyl-indan-1-yl)-3,3-dimethyl-piperazine with D-(−)-tartaric acid.

Thus, in one embodiment, the present invention relates to a process for the manufacture of 1-((1R,3S)-6-Chloro-3-phenyl-indan-1-yl)-3,3-dimethyl-piperazine or a pharmaceutically acceptable salt thereof comprising the step of mixing trans 1-(6-chloro-3-phenyl-indan-1-yl)-3,3-dimethyl-piperazine with D-(−)-tartaric acid in a polar solvent to obtain 4-((1R,3S)-6-Chloro-3-phenyl-indan-1-yl)-3,3-dimethyl-piperazine or a pharmaceutically acceptable salt thereof.

In a further embodiment, the mixture of trans 1-((6-chloro-3-phenyl-indan-1-yl)-3,3-dimethyl-piperazine and D-(−)-tartaric acid in a polar solvent is brought into conditions suitable for obtaining a solution of the trans 1-((6-chloro-3-phenyl-indan-1-yl)-3,3-dimethyl-piperazine and D-(−)-tartaric acid. Preferably, said mixture of trans 1-((6-chloro-3-phenyl-indan-1-yl)-3,3-dimethyl-piperazine and D-(−)-tartaric acid in a polar solvent is heated to an appropriate temperature to obtain a solution of the trans 1-((6-chloro-3-phenyl-indan-1-yl)-3,3-dimethyl-piperazine and D-(−)-tartaric acid.

In another embodiment, the present invention relates to a process for the manufacture of 1-((1R,3S)-6-Chloro-3-phenyl-indan-1-yl)-3,3-dimethyl-piperazine or a pharmaceutically acceptable salt thereof comprising the step of precipitating a product from a solution comprising trans 1-(6-chloro-3-phenyl-indan-1-yl)-3,3-dimethyl-piperazine and D-(−)-tartaric acid in a polar solvent to obtain 1-((1R,3S)-6-Chloro-3-phenyl-indan-1-yl)-3,3-dimethyl-piperazine or a pharmaceutically acceptable salt thereof.

In another embodiment, the present invention relates to, a process for the manufacture of 1-((1R,3S)-6-Chloro-3-phenyl-indan-1-yl)-3,3-dimethyl-piperazine or a pharmaceutically acceptable salt thereof comprising the steps of
a) mixing trans 1-(6-chloro-3-phenyl-indan-1-yl)-3,3-dimethyl-piperazine and D-(−)-tartaric acid in a polar solvent;
b) optionally heating the obtained mixture to an appropriate temperature to obtain a solution of the trans 1-((6-chloro-3-phenyl-indan-1-yl)-3,3-dimethyl-piperazine and D-(−)-tartaric acid;
c) cooling the solution obtained in b) until precipitation;
d) isolating the precipitate obtained in c);
e) optionally drying the precipitate obtained in d);
to obtain 1-((1R,3S)-6-Chloro-3-phenyl-indan-1-yl)-3,3-dimethyl-piperazine or a pharmaceutically acceptable salt thereof.

In a further embodiment, said process comprises a subsequent step in which the precipitate is recrystallised after step d) or e).

In a preferred embodiment, the trans 1-((6-chloro-3-phenyl-indan-1-yl)-3,3-dimethyl-piperazine used in the process for manufacture of 1-((1R,3S)-6-Chloro-3-phenyl-indan-1-yl)-3,3-dimethyl-piperazine is the trans racemic 1-((6-chloro-3-phenyl-indan-1-yl)-3,3-dimethyl-piperazine.

In one embodiment 1-((1R,3S)-6-Chloro-3-phenyl-indan-1-yl)-3,3-dimethyl-piperazine hemi D-(−)-tartrate is an intermediate or end product of the process. In a preferred embodiment, said 1-((1R,3S)-6-Chloro-3-phenyl-indan-1-yl)-3,3-dimethyl-piperazine hemi D-(−)-tartrate is in a crystalline form.

In one embodiment, the polar solvent applied in the processes of the present invention are chosen from water, a ketone, an alcohol, an organic acid or mixtures hereof such as water, acetone, ethanol, n-propanol, formic acid or mixtures hereof.

If a salt different from the chiral acid addition salt of the invention is desired, the purified chiral acid addition salt of Compound (I) or (II) may be used as starting material in further processes in which the chiral acid addition salt of the present invention is dissolved, the free base form is optionally obtained, and the desired salt, preferably a pharmaceutically acceptable salt is achieved by precipitation with an appropriate acid.

In one embodiment of the invention, the pharmaceutically acceptable salt is a succinate salt or a malonate salt. In one embodiment, the pharmaceutically acceptable salt is in the form of a crystalline hydrogen succinate salt of Compound (I) e.g., crystal form alpha or beta of the hydrogen succinate salt of Compound (I), or a crystalline hydrogen malonate salt of Compound (I). The succinate salt and malonate salt of Compound (I) are described in WO 2005/016900.

In another embodiment of the invention, the pharmaceutically acceptable salt is a tartrate salt or a malate salt. In one embodiment, the pharmaceutically acceptable salt is in the form of a crystalline hydrogen tartrate salt of Compound (II) or a hydrogen malate salt of Compound (II). The tartrate salt and malate salt of Compound (II) are described in WO 2006/086985.

All references cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various compounds of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The invention will be illustrated in the following non-limiting examples. All the examples described for manufacture of Compound (I) implies the use of L-(+)-tartaric acid as the chiral salt-forming acid. All the examples described for manufacture of Compound (II) implies the use of L(+)-tartaric acid and D(−)-tartaric acid.

EXAMPLES

HPLC Methods:

The chiral purity of 4-((1R,3S)-6-Chloro-3-phenyl-indan-1-yl)-1,2,2-trimethyl-piperazine was measured by chiral HPLC chromatography on a Chirapak ADH colomn 250×4.6 mm with an eluent: hexane/IPA/N-Ethylethanamine 90:10:0.2, column temperature: 35° C., flow: 0.4 mL/min and UV detection at 230 nm The retention times for the two enantiomers were 8.4 min for the (1S,3R)enantiomer and 9.3 min for Compound (I).

The chiral purity of 1-((1R,3S)-6-Chloro-3-phenyl-indan-1-yl)-3,3-dimethyl-piperazine was established by chiral HPLC chromatography on a Chirapak OD column 250×4.6 mm with an eluent: heptane/EtOH/DEA 98.4:1.5:0.1, column temperature: 35° C., flow: 1.0 mL/min and UV detection at 230 nm. The retention times for the two enantiomers 8.5 min for Compound (II) and 9.5 min for the (1S,3R)enantiomer.

Example 1

4-((1R,3S)-6-Chloro-3-phenyl-indan-1-yl)-1,2,2-trimethyl-piperazine L-(+)-tartrate, acetone Trans racemic 4-((6-Chloro-3-phenyl-indan-1-yl)-1,2,2-trimethyl-piperazine (3.0 g), was dissolved in acetone (100 mL). L-(+)-tartaric acid (1.3 g) was added and the suspension was heated to 50° C. until all tartaric acid had dissolved. The warm solution was left for cooling. Precipitation started after 15 minutes. The suspension was stirred overnight at room temperature and the product filtered off and dried in the hood at room temperature. Yield 2.00 g (91%).

The content of the two enantiomers were (1S,3R)enantiomer=4.6% and Compound (I)=95.4% corresponding to an ee=90.8% of 4-((1R,3S)-6-Chloro-3-phe nyl-indan-1-yl)-1, 2,2-trimethyl-piperazine L-(+)-tartrate.

The product (1.50 g) was recrystallised from ethanol (30 mL) at reflux. The solution was stirred overnight while cooled down to room temperature. The product was filtered off and dried in the hood at room temperature. Yield: 1.37 g (87%). The content of the two enantiomers were (1S,3R)enantiomer=0.8% and compound(I)=99.2% corresponding to an ee=98.4% of 4-((1R,3S)-6-Chloro-3-phe nyl-indan-1-yl)-1, 2,2-trimethyl-piperazine L-(+)-tartrate Example 2

4-((1R,3S)-6-Chloro-3-phenyl-indan-1-yl)-1,2,2-trimethyl-piperazine L-(+)-tartrate, ethanol Trans racemic 4-((6-Chloro-3-phenyl-indan-1-yl)-1,2,2-trimethyl-piperazine (1.5 g) was resolved with L-(+)-tartaric acid (0.63 g) from ethanol (50 mL). Yield 0.92 g (87%), (1S,3R)enantiomer=0.8% and Compound (I)=99.2% corresponding to an ee=98.4% of 4-((1R,3S)-6-Chloro-3-phenyl-indan-1-yl)-1,2,2-trimethyl-piperazine L-(+)-tartrate Example 3

4-((1R,3S)-6-Chloro-3-phenyl-indan-1-yl)-1,2,2-trimethyl-piperazine L-(+)-tartrate, propanol Trans racemic 4-((6-Chloro-3-phenyl-indan-1-yl)-1,2,2-trimethyl-piperazine (0.75 g) was resolved with L-(+)-tartaric acid (0.32 g) from propanol (25 mL). Yield 0.49 g (89.1%), (1S,3R)enantiomer=2.2% and Compound (I)=97.8% corresponding to an ee=95.6% of 4-((1R,3S)-6-Chloro-3-phenyl-indan-1-yl)-1,2,2-trimethyl-piperazine L-(+)-tartrate Example 4

4-((1R,3S)-6-Chloro-3-phenyl-indan-1-yl)-1,2,2-trimethyl-piperazine L-(+)-tartrate, ethanol and formic acid Trans racemic 4-((6-Chloro-3-phenyl-indan-1-yl)-1,2,2-trimethyl-piperazine (1.5 g) was resolved with L-(+)-tartaric acid (0.38 g) and formic acid (0.097 g) from ethanol (50 mL). Yield 0.56 g (51%), (1S,3R)enantiomer=4.8% and Compound (I)=95.2% corresponding to an ee=90.4% of 4-((1R, 3S)-6-Chloro-3-phenyl-indan-1-yl)-1,2,2-trimethyl-piperazine L-(+)-tartrate Example 5

4-((1R,3S)-6-Chloro-3-phenyl-indan-1-yl)-1,2,2-trimethyl-piperazine L-(+)-tartrate, ethanol Trans racemic 4-((6-Chloro-3-phenyl-indan-1-yl)-1,2,2-trimethyl-piperazine (1.5 g) was resolved with L-(+)-tartaric acid (0.95 g) from ethanol (50 mL). Yield 0.82 g (77%), (1S,3R)enantiomer=3.2% and Compound (I)=96.8% corresponding to an ee=93.6% of 4-((1R,3S)-6-Chloro-3-phenyl-indan-1-yl)-1,2,2-trimethyl-piperazine L-(+)-tartrate Example 6

1-((1R,3S)-6-Chloro-3-phenyl-indan-1-yl)-3,3-dimethyl-piperazine hemi L-(+)-tartrate, acetone Trans racemic 1-(6-Chloro-3-phenyl-indan-1-yl)-3,3-dimethyl-piperazine) (2.9 g) was dissolved in acetone (200 mL). L-(+)-tartaric acid (1.3 g) was added and the suspension heated to reflux until almost all had dissolved. A slight turbidity resided, which was filtered off in a folded paper filter. The warm solution was left for cooling to room temperature and precipitation started very slowly after an hour. The suspension was stirred overnight at room temperature, and the product was filtered off, very slowly, and dried in the hood at room temperature. Yield 2.74 g (65%). The content of the two enantiomers were Compound (II)=58.6% and (1S,3R)enantiomer=41.4% corresponding to an ee=17.2% of 1-((1R,3S)-6-chloro-3-phenyl-indan-1-yl)-3,3-dimethyl-piperazine hemi L-(+)-tartrate.

The product (2.00 g) was recrystallised from a mixture of ethanol (100 mL) and water (10 mL) at reflux. The solution was stirred while cooled down to room temperature and stirred for a week at room temperature. The precipitate was filtered off and dried in the hood at room temperature. Yield 0.81 g (40.5%). The content of the two enantiomers were Compound (II)=3.9% and (1S,3R)enantiomer=96.1% corresponding to an ee=92.2% of 1-((1S,3R)-6-Chloro-3-phenyl-indan-1-yl)-3,3-dimethyl-piperazine hemi L-(+)-tartrate i.e. the recrystallisation from aqueous ethanol have reversed the most abundant of the enantiomers giving a yield of 53% when the content of the chiral antipodes in the starting material are taken into account.

Example 7

1-((1S,3R)-6-Chloro-3-phenyl-indan-1-yl)-3,3-dimethyl-piperazine hemi L-(+)-tartrate, ethanol Trans racemic 1-(6-Chloro-3-phenyl-indan-1-yl)-3,3-dimethyl-piperazine (2.9 g) was resolved with L-(+)-tartaric acid (1.3 g) from ethanol (350 mL). Yield 1.49 g (42%), Compound (II)=2.8% and (1S,3R)enantiomer=97.2% corresponding to an ee=94.4% of 1-((1S,3R)-6-Chloro-3-phenyl-indan-1-yl)-3,3-dimethyl-piperazine hemi L-(+)-tartrate.

Example 8

1-((1S,3R)-6-Chloro-3-phenyl-indan-1-yl)-3,3-dimethyl-piperazine hemi L-(+)-tartrate, acetone Trans racemic 1-(6-Chloro-3-phenyl-indan-1-yl)-3,3-dimethyl-piperazine (0.85 g) was resolved with L-(+)-tartaric acid (0.37 g) from acetone (25 mL) and water (2.5 mL). Yield 0.61 g (51%), Compound (II)=49.8% and (1S,3R)enantiomer=50.2% corresponding to an ee=0.4% i.e. the racemate.

Example 9

1-((1S,3R)-6-Chloro-3-phenyl-indan-1-yl)-3,3-dimethyl-piperazine hemi L-(+)-tartrate, ethanol Trans racemic 1-(6-Chloro-3-phenyl-indan-1-yl)-3,3-dimethyl-piperazine (1.45 g) was resolved with L-(+)-tartaric acid (0.65 g) from ethanol (50 mL). Yield 0.62 g (56%), Compound (II)=2.2% and (1S,3R)enantiomer=97.8% corresponding to an ee=95.6% of 1-((1S,3R)-6-Chloro-3-phenyl-indan-1-yl)-3,3-dimethyl-piperazine hemi L-(+)-tartrate.

Example 10

1-((1R,3S)-6-Chloro-3-phenyl-indan-1-yl)-3,3-dimethyl-piperazine hemi D-(−)-tartrate, ethanol and formic acid Trans racemic 1-(6-Chloro-3-phenyl-indan-1-yl)-3,3-dimethyl-piperazine (1.5 g) was resolved with D-(−)-tartaric acid (0.40 g) and formic acid (0.10 mL) from ethanol (50 mL). Yield 0.78 g (71%), Compound (II)=99.0% and (1S,3R)enantiomer=1.0% corresponding to an ee=98.0% of 1-((1R,3S)-6-Chloro-3-phenyl-indan-1-yl)-3,3-dimethyl-piperazine hemi D-(−)-tartrate.

Example 11

1-((1R,3S)-6-Chloro-3-phenyl-indan-1-yl)-3,3-dimethyl-piperazine D-(−)-tartrate, ethanol Trans racemic 1-(6-Chloro-3-phenyl-indan-1-yl)-3,3-dimethyl-piperazine (0.94 g) was resolved with D-(−)-tartaric acid (0.94 g) from ethanol (150 mL). Yield 0.61 g (59%), compound(II)=98.3% and (S1,R3)enantiomer=1.7% corresponding to an ee=96.6% of 1-((1R,3S)-6-Chloro-3-phenyl-indan-1-yl)-3,3-dimethyl-piperazine hemi D-(−)-tartrate.

The invention claimed is:

1. A process for the manufacture of 4-((1R,3S)-6-chloro-3-phenyl-indan-1-yl)-1,2,2-trimethyl-piperazine or a pharmaceutically acceptable salt thereof comprising the step of mixing trans 4-(6-chloro-3-phenyl-indan-1-yl)-1,2,2-trimethyl-piperazine with L-(+)-tartaric acid in water to obtain 4((-1R,3S)-6-chloro-3-phenyl-indan-1-yl)-1,2,2-trimethyl-piperazine or a pharmaceutically acceptable salt thereof.

2. The process according to claim 1, wherein the mixture of trans 4-(6-chloro-3-phenyl-indan-1-yl)-1,2,2-trimethyl-piperazine and L-(+)-tartaric acid in water is brought into conditions suitable for obtaining a solution of the trans 4-(6-chloro-3-phenyl-indan-1-yl)-1,2,2-trimethyl-piperazine and L-(+)-tartaric acid.

3. The process according to claim 1, wherein the mixture of trans 4-(6-chloro-3-phenyl-indan-1-yl)-1,2,2-trimethyl-piperazine and L-(+)-tartaric acid in water is heated to an appropriate temperature to obtain a solution of the trans 4-(6-chloro-3-phenyl-indan-1-yl)-1,2,2-trimethyl-piperazine and L-(+)-tartaric acid.

4. A process for the manufacture of 4((1R,3S)-6-chloro-3-phenyl-indan-1-yl)-1,2,2-trimethyl-piperazine or a pharmaceutically acceptable salt thereof comprising the step of precipitating a product from a solution comprising trans 4-(6-chloro-3-phenyl-indan-1-yl)-1,2,2-trimethyl-piperazine and L-(+)-tartaric acid in water to obtain 4-((1R,3S)-6-chloro-3-phenyl-indan-1-yl)-1,2,2-trimethyl-piperazine or a pharmaceutically acceptable salt thereof.

5. A process for the manufacture of 4-((1R,3S)-6-chloro-3-phenyl-indan-1-yl)-1,2,2-trimethyl-piperazine or a pharmaceutically acceptable salt thereof comprising the steps of
a) mixing trans 4-(6-chloro-3-phenyl-indan-1-yl)-1,2,2-trimethyl-piperazine and L-(+)-tartaric acid in water;
b) optionally heating the obtained mixture to an appropriate temperature to obtain a solution of the trans 4-(6-chloro-3-phenyl-indan-1-yl)-1,2,2-trimethyl-piperazine and L-(+)-tartaric acid;
c) cooling the solution obtained in b) until precipitation;
d) isolating the precipitate obtained in c);
e) optionally drying the precipitate obtained in d);
to obtain 4(1R,3S)-6-chloro-3-phenyl-indan-1-yl)-1,2,2-trimethyl-piperazine or a pharmaceutically acceptable salt thereof.

6. The process according to claim 5 which process comprises a subsequent step in which the precipitate is recrystallised after step d) or e).

7. The process according to claim 6, wherein said trans 4-(6-chloro-3-phenyl-indan-1-yl)-1,2,2-trimethyl-piperazine is the trans racemic 4-(6-chloro-3-phenyl-indan-1-yl)-1,2,2-trimethyl-piperazine.

8. The process according to claim 7, wherein 4-((1R,3S)-6-chloro-3-phenyl-indan-1-yl)-1,2,2-trimethyl-piperazine L-(+)-tartrate is an intermediate or end product of the process.

9. The process according to claim 8, wherein said 4-((1R,3S)-6-chloro-3-phenyl-indan-1-yl)-1,2,2-trimethyl-piperazine L-(+)-tartrate is obtained in a crystalline form.

10. The compound 4-((1R,3S)-6-chloro-3-phenyl-indan-1-yl)-1,2,2-trimethyl-piperazine L-(+)-tartrate wherein the compound is in a crystalline form.

11. A process for the manufacture of 1-((1R,3S)-6-chloro-3-phenyl-indan-1-yl)-3,3-dimethyl-piperazine or a pharmaceutically acceptable salt thereof comprising the step of mixing trans 1-(6-chloro-3-phenyl-indan-1-yl)-3,3-dimethyl-piperazine with D-(−)-tartaric acid in water to obtain 1((1R,3S)-6-chloro-3-phenyl-indan-1-yl)-3,3-dimethyl-piperazine or a pharmaceutically acceptable salt thereof.

12. The process according to claim 11, wherein the mixture of trans 1-((6-chloro-3-phenyl-indan-1-yl)-3,3-dimethyl-piperazine and D-(−)-tartaric acid in water is brought into conditions suitable for obtaining a solution of the trans 1-((6-chloro-3-phenyl-indan-1-yl)-3,3-dimethyl-piperazine D-(−)-tartaric acid.

13. The process according to claim 11, wherein the mixture of trans 1-((6-chloro-3-phenyl-indan-1-yl)-3,3-dimethyl-piperazine and D-(−)-tartaric acid in water is heated to an appropriate temperature to obtain a solution of the trans -((6-chloro-3-phenyl-indan-1-yl)-3,3-dimethyl-piperazine and D-(−)-tartaric acid.

14. A process for the manufacture of 1-((1R,3S)-6-chloro-3-phenyl-indan-1-yl)-3,3-dimethyl-piperazine or a pharmaceutically acceptable salt thereof comprising the steps of
a) mixing trans 1-(6-chloro-3-phenyl-indan-1-yl)-3,3-dimethyl-piperazine and D-(−)-tartaric acid in water;
b) optionally heating the obtained mixture to an appropriate temperature to obtain a solution of the trans 1-((6-chloro-3-phenyl-indan-1-yl)-3,3-dimethyl-piperazine and D-(−)-tartaric acid;
c) cooling the solution obtained in b) until precipitation;
d) isolating the precipitate obtained in c);
e) optionally drying the precipitate obtained in d);
to obtain 1-((1R,3S)-6-chloro-3-phenyl-indan-1-yl)-3,3-dimethyl-piperazine or a pharmaceutically acceptable salt thereof.

15. The process according to claim 14 which process comprises a subsequent step in which the precipitate is recrystallised after step d) or e).

16. The process according to claim 15, wherein said trans 1-((6-chloro-3-phenyl-indan-1-yl)-3,3-dimethyl-piperazine is the trans racemic 1-((6-chloro-3-phenyl-indan-1-yl)-3,3-dimethyl-piperazine.

17. The process according to claim 16, wherein 1-((1R, 3S)-6-chloro-3-phenyl-indan-1-yl)-3,3-dimethyl-piperazine hemi D-(−)-tartrate is an intermediate or end product of the process.

18. The process according to claim 17, wherein said 1-((1R,3S)-6-chloro-3-phenyl-indan-1-yl)-3,3-dimethyl-piperazine hemi D-(−)-tartrate is obtained in a crystalline form.

* * * * *